United States Patent [19]
Doundoulakis

[11] Patent Number: 4,974,615
[45] Date of Patent: Dec. 4, 1990

[54] ELASTIC FILAMENT FOR ORAL HYGIENE

[76] Inventor: George J. Doundoulakis, 2498 Kayron La., North Bellmore, N.Y. 11710

[21] Appl. No.: 385,051

[22] Filed: Jul. 26, 1989

[51] Int. Cl.⁵ ............................................. A61C 15/00
[52] U.S. Cl. ..................................................... 132/321
[58] Field of Search ............... 132/321, 323, 324, 325, 132/326, 327, 329

[56] References Cited

U.S. PATENT DOCUMENTS

| | | | |
|---|---|---|---|
| 1,287,926 | 12/1918 | Ecaubert | 132/325 |
| 1,989,895 | 2/1935 | Van Gilder | 132/323 |
| 2,522,794 | 9/1950 | Medof | 132/325 |
| 2,612,177 | 9/1952 | Footer | 132/324 |
| 2,821,202 | 1/1958 | Davis | 132/329 |
| 3,247,857 | 4/1966 | Kanbar | 132/329 |
| 3,491,776 | 1/1970 | Fleming | 132/321 |
| 3,511,249 | 5/1970 | Baitz | 132/329 |
| 4,265,258 | 5/1981 | Eaton, II | 132/321 |
| 4,270,556 | 6/1981 | McAllister | 132/321 |
| 4,519,408 | 5/1985 | Charatan | 132/321 |
| 4,550,741 | 11/1985 | Krag | 132/321 |
| 4,836,226 | 6/1989 | Wokak | 132/321 |

Primary Examiner—John J. Wilson
Assistant Examiner—Frank A. Laviola, Jr.

[57] ABSTRACT

A filamentary article (8) free of silk-like fibers is disclosed, made out of an elastomeric material for use in dental hygiene. The article (8) is stretchable for proportionately reducing its cross section so that a sector (1) thereof, can enter between the teeth. The article (8) provides cuts along the edge, is twisted, or knotted at predetermined intervals along its length for furnishing radially directed edges or surfaces to help wipe food remanants, when longitudinally drawn through the larger interproximal openings, usually found in between teeth near the gums.

6 Claims, 1 Drawing Sheet

ELASTIC FILAMENT FOR ORAL HYGIENE

DESCRIPTION

1. Technical Field

The present invention relates to a dental floss-like tooth cleaner and in particular to a novel elastic filament cleaner, which is to be used for the same purpose as dental floss, but in a more efficient manner, for removing food remnants from the interproximal spaces in between teeth.

2. Background and Prior Art

Food particles and fibers from food, wedged in the spaces between teeth provide fertile ground for the growth of bacteria, which can contribute to mouth odor and to decay of the teeth and gums. Toothpastes are extensively used with the help of toothbrushes for the purpose of removing residual food particles from teeth. While the toothbrush does remove substantial amounts of such particles, the brush is ineffective in removing food particles and fibers which are wedged between teeth. Dental floss made out of silk-like thread is often forced through the interproximal spaces in between teeth for removal of such particles and fibers.

The drawbacks with the silk-like dental floss are:

(1) The conventional dental floss is a relatively rigid body, as far as its diameter is concerned, so that it often cannot fit to enter between the teeth. This is especially true with the waxed dental floss, where the wax has added to its diameter and rigidity.

(2) The non-waxed dental floss, having a smaller diameter can enter easier through narrower spacing between teeth, but it is not as effective in removing food particles in the case of wider spacing between teeth; because of its small diameter and hardness of its material it provides a sharp enough edge to inflict cuts on to the gums.

(3) The conventional dental floss, whether the waxed or the non-waxed kind, often breaks up into fine silk-like fibers, especially when it encounters sharp tooth edges or rough and/or sharp restorations. Such fibers then, usually get entangled with, or wedged between the teeth.

(4) Because of the dental floss's slippery surface and small cross section and because it does not provide surfaces normal to its axis, it is ineffective in removing particles when it is drawn longitudinal (in the direction of its axis), as it would be needed for the removal of residual particles from larger openings, usually occurring between teeth, next to the gums. Presently the user holds the dental floss tensioned between two fingers, one of each hand, which he moves to impart to the dental floss only a motion transverse to its axis, up and down, along the side of the teeth. The available longitudinal motion of the dental floss is not being used.

DESCRIPTION OF THE PRESENT INVENTION

The present invention provides for an elastic dental filament instead of dental floss, made out of an elastomeric material, so that when stretched, its diameter can decrease for the filament to enter in the narrow available spaces between teeth. As the elastic filament is then driven along a space between teeth. with the tension relaxed, it is capable of automatically adjusting its diameter to the width of the particular space between the teeth; thereby being more effective in wiping food particle and even bacteria away from the surface of the teeth.

The invention further provides for surface discontinuities or for radial enlargements in the normal filament diameter, at predetermined intervals along the length of the dental filament for contributing wiping and/or brushing action inside the wider openings usually located between the teeth near the gums, for removal of food remnants as the dental filament is drawn longitudinally through such openings.

Three embodiments are presented to illustrate various methods for implementing surfaces normal to the axis of the elastic dental filament. The method characterizing Embodiment A provides for a thin flat filament which has been twisted during manufacture. Such an elastic dental filament can be soft and yielding to the shape of the opening between teeth, while providing the radial surface elements needed for removing food remnants from the spaces between teeth, acting like a screw drawn in the direction of its axis without being rotated. Other species in this embodiment provide on the surface of the filament, for cuts or holes, which can render similar action.

Embodiment B is characterized by a second method for providing radial surface elements in the elastic dental filament in terms of knots tied out of the filament itself at predetermined intervals along its length. At least two types of knots, constituting species of Embodiment B, are shown. The knots may be chosen to be releasable if excessive force is applied as they are pulled through the tooth space; or the knots may be locked by use of cement or by insertion of a bunch of short lengths of hair-like elastomeric filaments, which can further provide brushing action inside the tooth opening.

Embodiment C is characterized by a third method for providing radially directed surface elements in the elastic dental filament through shaped radial enlargements, such as small globules, cylindroids, or other special shapes of radial enlargements at predetermined intervals along the length of the elastic dental filament.

It may be noted that as the elastic dental filament contains no silk-like fibers it cannot be shredded into such fibers by sharp edges of the teeth or restorations.

It is the main object of the present invention to provide an elastic filament for dental hygiene for use in a similar manner as the conventional dental floss is being used to remove food remnants from the interproximal spaces in between the teeth; but being free of silk like fibers, while it is capable of more extensive service and of improved performance over the conventional dental floss.

It is, an object of the present invention to provide an elastic dental filament so that its diameter can vary and thus accommodate the variable spacing between teeth; thereby being more effective than conventional dental floss when moved transversely along the space between teeth, as the conventional dental floss is presently used.

It is another object of the present invention to provide an elastic dental filament with radial surface elements, for the purpose of engaging and wiping food remnants when the filament is drawn longitudinally through the larger openings usually occurrig between teeth near the gums; thereby providing brushing action inside such openings, constituting a new dimension in dental cleaning.

Other objects and features of the invention will be discussed as the description of the particular physical embodiments are selected to illustrate the invention processes. The various novel features that characterize the invention are pointed out particularly in the claims annexed to and forming a part of this specification. In addition, for a better understanding of the invention, its operating advantages and specific objects attained by its use, references are made to the accompanying drawings and descriptive matter in which preferred embodiments of the invention are illustrated and described.

The invention is illustrated diagrammatically in the accompanying drawings by way of examples. The diagrams illustrate only the principles of the invention and how these principles are employed in various fields of application. It is, however to be understood that the purely diagrammatic showing does not offer a survey of other possible constructions, and a departure from the constructional features, diagrammatically illustrated, does not necessarily imply a departure from the principles of the invention. For example, the elastic dental filament itself may be coiled or bunched during manufacture to provide radially directed surface elements for engagement with the food remnants as it is drawn longitudinally through the spaces between teeth.

It is, therefore to the understood that the invention is capable of numerous modifications and variations to those skilled in the art without departing from the spirit and scope of the invention.

In the accompanying drawings, forming part hereof, similar reference characters designate corresponding parts.

BRIEF DESCRIPTION OF DRAWINGS

The details of my invention will be described in connection with the accompanying drawings in which.

BEST MODE FOR CARRYING OUT THE INVENTION

Figure 1A:
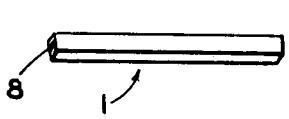
FIG. 1(a, b, c) is a perspective sectional elevation view of sections of an elastic filament representing species in accordance with Embodiment A of the invention, comprising a substantially rectangular cross section, with FIG. 1(b) showing holes punched on its surface and FIG. 1(c) showing cuts along the edges of the filament.
Figure 1B:
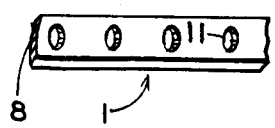
Figure 1C:
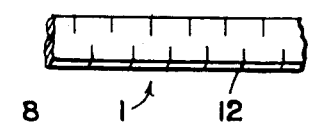
Figure 2:
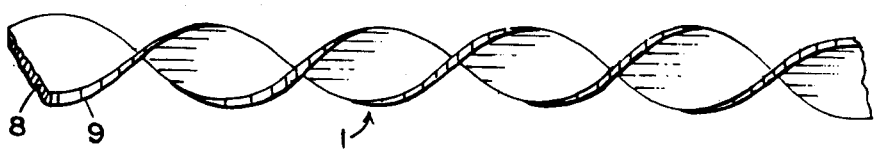
FIG. 2 is a perspective elevation view showing still another species of Embodiment A of a novel elastic dental filament, comprising a substantially rectangular cross section, which has been twisted along its length during manufacture to provide radially directed surface elements.

Embodiment A is presented in terms of elastic filaments, where slender extrusion of an elastomeric material with a predetermined cross section is marketed as is, or after being twisted or with holes or cuts added to it, as shown in the species which are illustrated in FIGS. 1 and 2.

Referring to FIG. 1(a), the dental filament 1 is shown to comprise a length of elastomeric material extruded as a fine thread-like structure with a round or rectangular cross-section. The filament is then to be marketed as is without further processing except packaging. If a rectangular cross section is chosen for the filament, the ratio of thickness to width can be established by the manufacturer. In FIG. 1(a) this ratio is shown to be substantially unity. In FIG. 1(b) the width to thickness ratio is shown to be greater than 1 so that the width will be sufficient to accommodate holes 11 at predetermined intervals along the length of the filament. The holes 11 can be effective in two ways: (1) the edge contributed by the holes can provide wiping action along the edge of the teeth as the filament is moved both transversely or drawn longitudinally through the space between teeth. and (2) the holes provide space where food remnants can be entrapped as the filament undergoes above motions. FIG. 1(c) shows surface discontinuities to be provided on the filament in terms of simple cuts 12, for contributing brushing action along the edges of teeth when the filament is drawn longitudinally through a space between teeth.

Referring to FIG. 2, the elastic dental filament 1 is shown to have a substantially rectangular cross section which has been rotated along its length, generating a twisted surface resembling a twisted rubber band. The intended thickness, however, is only about ¼ that of a conventional rubber band. One way this filament can be done is to have it extruded while the extrusion die is being rotated. In such a set-up, the extruded filament can be allowed to travel through a substantial height so that it can cool by the time it reaches the floor where it can be wound into spools, in a fashion similar to that used for the production of fiberglass. If desirable the filament 1 may be subjected to radial cuts (not shown), similar to those shown in FIG. 1(c), so that the filament can also act like a twisted brush as is longitudinally drawn through the larger interproximal spaces.

Figure 3:
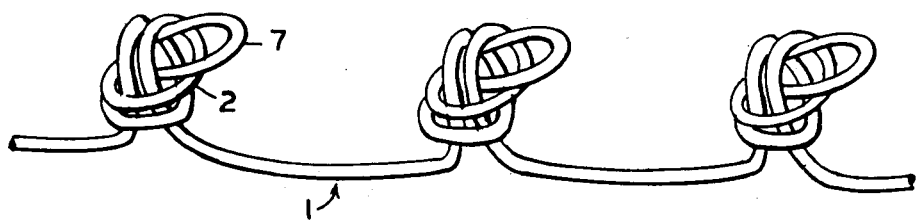
FIG. 3 is a perspective elevation view of an elastic dental filament according to Embodiment B of the invention, comprising knots at predetermined intervals along its length, as the means for interacting and wiping out food remnants from openings between teeth.
Figure 4:
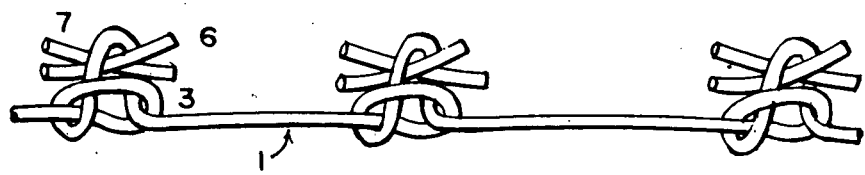
FIG. 4 is a perspective elevation view of a second species of Embodiment B of an elastic dental filament, similar to that in FIG. 3, with a different type of knot, here shown locked with a bunch of short pieces of elastic fiber, for providing brushing action in removing food remnants from larger openings in between teeth.

Embodiment B is illustrated in terms of two species shown in FIGS. 3 and 4 showing the fiber 1 being itself tied into knots 2 and 3, respectively. The knot 2 is a stable knot but, unless cemented, it could release if subjected to a strong resistance as is being pulled through a tooth opening, but with no harm done. The knot 3 of FIG. 4 is a less stable knot but it can acquire additional stability if locked, as shown, by short piece of elastic filament, which may also serve as wiping hair to provide additional brushing action inside a larger tooth opening. It may be noted that a similar locking with short pieces of filament can be used in conjunction with knot 2 of FIG. 3 by insertion of short pieces of elastic filament inside the loop 7, generating a more massive and more stable knot. While the knots 2 and 3 appear to be massive due to the large scale in which they are drawn, in actuality they may be tiny. For example, when latex thread of 0.015 inch diameter was used the thickness of the knot 2 turned out to be 0.030 inches thick. There are commercially available latex threads of less than 0.003 inches in diameter, at which thickness a knot can be made having a plurality of loops in the form of a bowknot, and still remain small enough to pass through the openings of the teeth with relatively small force. It may further be noted that the thickness of the main filament 1 can be more substantial than those of the short filament pieces, which can be as thin as the hair of a brush. The short elastic pieces or the knots themselves, can be secured, if desirable, by drops of proper cement.

Embodiment C includes species in which the diameter varies to form enlargments of predetermined shape, which can be accommodating to the shape of larger openings between teeth, and also be effective in removing food remnants from such openings. Two examples of such species are shown in terms of the species in FIGS. 5 and 6.

Figure 5:
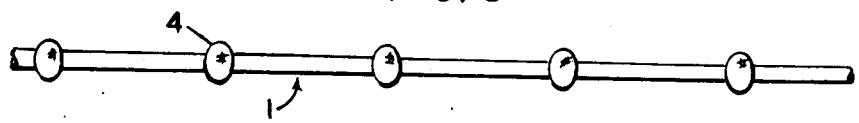
FIG. 5 is a perspective elevation view of a species of Embodiment C of the elastic dental filament, comprising spherical radial enlargements at predetermined intervals, as the means for interacting and wiping out food remnants from larger openings between teeth.

FIG. 5 shows a species where sections of the string at predetermined interval are increased in diameter to form substantially round enlargements 4.

Figure 6:
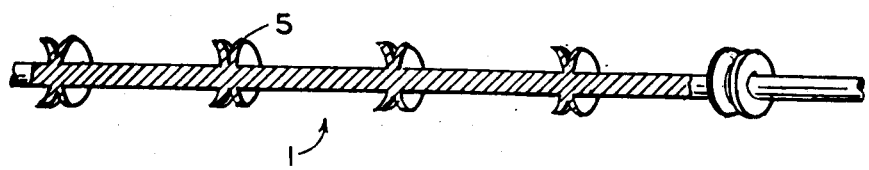
FIG. 6 is a perspective elevation cross sectional view of another species of Embodiment C of an elastic dental filament, similar to that in FIG. 5, here showing cylindroidal radial enlargements for interacting and wiping out food remnants from openings between teeth.

FIG. 6 illustrates a second example of a radial enlargements 5, of a cylindroidal shape that can provide good scraping qualities and flexibility, so that they can easily deform to adapt to the particular shape of the interproximal opening. Around the periphery the shape can be continuous, as shown in FIG. 6, or it may break into a number of radial rays, (not shown) for further flexibility and effectiveness. An easy way to manufacture such a filament cleaner would be to have the material being continuously extruded, vertically, while an opening and closing mold would be providing the desirable shape. Another possible way of implementing desirable radial enlargements in the dental filament would be to have the globules or cylindroids fabricated separately, then threaded and cemented at predetermined intervals onto the uniform filament.

I claim:

1. A filament comprising a slender structure and a generally uniform rectangular cross section for cleaning interproximal spaces between teeth and gums; said cross section comprising a narrow side determining its thickness and a wider side determining its width; wherein said filament is free of silk-like fibers, for cleaning teeth without leaving fibers behind; said filament being made out of an elastomeric material so it can be soft to gums and be stretchable for easy insertion between teeth along its narrow side; while its wider side wipes over the teeth of the interproximal space; and wherein said filament is further comprising surface discontinuity means in terms of cuts at least along a lower edge; thereby, such cuts providing edges which are effective in brushing out food remnants, especially in large interproximal spaces near the gums.

2. A filament comprising a slender structure and generally uniform cross section used in oral hygiene for cleaning interproximal spaces between teeth and gums; wherein said filament is free of silk-like fibers, for cleaning teeth without leaving fibers behind; said filament being made out of an elastomeric material so it can be soft to gums and be stretchable for easy insertion between teeth; wherein said filament further comprises releasable knot means at predetermined intervals along its length for providing wiping action to food remnants, as said filament is longitudinally drawn through larger interproximal openings, usually found in between teeth near the gums; wherein said releasable knot means can be made during manufacture at any point of said filament without the need of cutting said filament for passing ends through filament bights; thereby enabling easy manufacture of said filament of any desired length.

3. The elastic filament according to claim 2, wherein said releasable knot means are formed using a bight with double filament so that said knot means can withstand a predetermined force of resistance by teeth and gums before unravel, as said filament is being longitudinally pulled through interproximal spaces.

4. The elastic filament according to claim 3 wherein said knot means further comprises knot locking means for preventing said knot means from being released under the force of resistance encountered by said filament due to friction against teeth and gums as said filament is being pulled through interproximal spaces.

5. The elastic filament according to claim 4, wherein said knot locking means comprises cement means, for holding said knot means in tact, and not being released, when a force of resistance is encountered as said filament is longitudinally drawn through interproximal spaces.

6. The elastic filament according to claim 4, wherein said knot locking means comprises short pieces of elastic filament; thereby such elastic pieces, while preventing said knot means from unraveling under a force of resistance by teeth and gums as said filament is being longitudinally pulled through interproximal spaces, they also provide brushing action to food remnants.

* * * * *